United States Patent [19]
Koenig

[11] Patent Number: 5,973,200
[45] Date of Patent: Oct. 26, 1999

[54] PROCESS FOR THE PREPARATION OF 2-HYDROXY-4-(METHYLTHIO) BUTANOIC ACID OR METHIONINE BY MERCAPTAN ADDITION

[75] Inventor: Karl E. Koenig, Wildwood, Mo.

[73] Assignee: Novus International, Inc., St. Louis, Mo.

[21] Appl. No.: 09/009,275

[22] Filed: Jan. 20, 1998

Related U.S. Application Data

[60] Provisional application No. 60/037,657, Jan. 23, 1997.
[51] Int. Cl.$^6$ ................................................. C07C 315/00
[52] U.S. Cl. ..................... 562/581; 562/556; 560/183; 558/436; 558/441; 568/41
[58] Field of Search ...................... 562/556, 581; 560/183; 568/41; 558/436, 441

[56] References Cited

U.S. PATENT DOCUMENTS

| | | |
|---|---|---|
| 2,675,392 | 4/1954 | Theobald . |
| 3,466,322 | 9/1969 | Elam . |
| 3,699,148 | 10/1972 | Darcas et al. . |
| 3,884,951 | 5/1975 | Oswald . |
| 3,998,866 | 12/1976 | Oswald . |
| 4,082,795 | 4/1978 | Brace . |

FOREIGN PATENT DOCUMENTS

| | | |
|---|---|---|
| 8157447 | 6/1996 | Japan . |

OTHER PUBLICATIONS

Alden, et al. "Free–radical Reactions of Halogenated Bridged Polycyclic Compounds. Part III. The Free–radical Addition of Alkanethiols, Bromotrichloromethane, and Bromine to Hexachloromethylenenorbornene," J. Chem. Soc. (C), pp. 1017–1020, 1967.

Alden, et al. "Free–radical Reactions of Halogenated Bridged Polycyclic Compounds. Part IV. The Free–radical Addition of Polyhalogenomethanes and of Thiols to 2,3–Dichloronorborna–2,5–diene, and the Preparation of 2,3–Dichloroquadricyclene," J. Chem. Soc. (C), pp. 2007–2011, 1967.

Balla, et al. "Kinetics of the Reaction of $CH_3S$ with Unsaturated Hydrocarbons," J. Am. Chem. Soc., vol. 109, No. 16, pp. 4804–4808, 1987.

Kamel Boustany "Chemistry of Sulfur Compounds: Selectivity of Addition of Thiyl Radicals to Terminal Olefins," Journal of Chemical and Engineering Data, vol. 17, No. 1, pp. 104–106, 1972.

Davies, et al. "Some Free–radical Addition Reactions of Norbornene and Related Compounds,"J. Chem. Soc. (C), pp. 1585–1590, 1969.

Grattan, et al. "Free–radical Addition of Alkanethiols to Some Acyclic Olefins," J. Chem. Soc. Perkin Transactions I, pp. 2264–2267, 1973.

Radchenko, et al. "Free–radical Addition of Mercaptans to Alkylthiovinylacetylene and Their Analogs," Zh. Org. Khim., vol. 10, No. 11, pp. 2456–2457, 1974. (Abstract only).

Sato, et al. "Polyaddition of Diallenes: Radical Polyaddition of Dithiols to 1,4–Bis(allenyloxy)benzene," Macromolecules, vol. 26, No. 19, pp. 5185–5186, 1993.

Sato, et al. "Radical Polyaddition of Dithiols to Bis(alkoxyallene)s," Macromolecules, vol. 26, No. 19, pp. 5187–5191, 1993.

Steadman, et al. "A Methionine Substitute: 4–Methylthiobutane–1,2–diol," J. Agric. Food Chem., vol. 23, No. 6, pp. 1137–1144, 1975.

Broxterman, et al. "Synthesis of (Optically Active) Sulfur–Containing Trifunctional Amino Acids by Radical Addition to (Optically Active) Unsaturated Amino Acids" Journal of Organic Chemistry, vol. 57, No. 23, pp. 6286–6294, 1992.

*Primary Examiner*—Paul J. Killos
*Attorney, Agent, or Firm*—Senniger, Powers, Leavitt & Roedel

[57] ABSTRACT

A process for the free-radical addition of a mercaptan to a nonconjugated olefinic substrate having a terminal carbon-carbon double bond is disclosed. 2-Hydroxy-4-(ethylthio) butanoic acid (HMBA) or methionine can be prepared using this method. The nonconjugated olefinic substrate has the general formula:

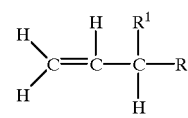

wherein R is selected from the group consisting of —COOH, —COOR$^2$, —CONR$^3$R$^4$, —CN and —CCl$_3$, R$^1$ is selected from the group consisting of —OH, —OCOR$^2$, —NHCOR$^2$ and —NH$_2$, R$^2$ is selected from the group consisting of alkyl, cycloalkyl and aryl and R$^3$ and R$^4$ are independently selected from the group consisting of —H and R$^2$.

11 Claims, No Drawings

PROCESS FOR THE PREPARATION OF 2-HYDROXY-4-(METHYLTHIO) BUTANOIC ACID OR METHIONINE BY MERCAPTAN ADDITION

This application claims the benefit of U.S. provisional application Ser. No. 60/037,657, filed Jan. 23, 1997, the disclosure of which is expressly incorporated herein by reference.

BACKGROUND OF THE INVENTION

The present invention relates generally to a process for the preparation of a mercaptan addition product. More particularly, the present invention relates to a process for the preparation of a mercaptan addition product by the free-radical addition of a mercaptan to selected nonconjugated olefinic substrates having a terminal carbon-carbon double bond, the mercaptan adding across the terminal carbon-carbon double bond of the substrate. The process may be used to prepare 2-hydroxyl-4-(methylthio)butanoic acid (HMBA) (or methionine.

HMBA is the hydroxy analog of methionine, an essential amino acid commonly deficient in grains used in animal feed compositions. HMBA is a metabolite in methionine utilization, and is widely used as a methionine supplement in animal feed formulations.

One way of producing HMBA involves the Michael addition of methyl mercaptan to acrolein in the presence of an organic amine catalyst (e.g. pyridine) to produce 3-(methylthio)propanal (MMP). The MMP is then reacted with hydrogen cyanide in the presence of an organic amine catalyst (e.g., the same catalyst used in the olefin/mercaptan addition reaction) to produce 2-hydroxy-4-(methylthio) butanenitrile (HMBN). The HMBN is subsequently hydrolyzed to produce HMBA. This reaction sequence is shown below.

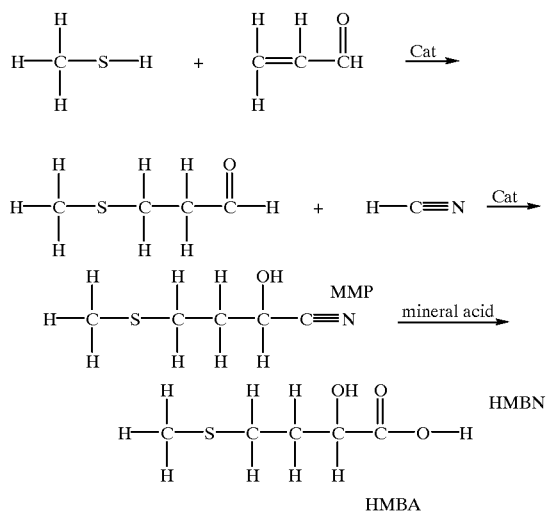

Although the above-described sequence has proven to be acceptable in the commercial preparation of HMBA, it would be highly beneficial to identify alternative synthesis routes for producing HMBA as well as methionine.

SUMMARY OF THE INVENTION

Among the objects of the present invention, therefore, are the provision of an alternative process for the preparation of HMBA or methionine; the provision of such a process capable of producing HMBA or methionine in high yield; the provision of such a process which utilizes available starting materials and that is adaptable to the commercial preparation of HMBA or methionine.

Briefly, therefore, the present invention is directed to a process for the preparation of a mercaptan addition product comprising free radical addition of methyl mercaptan to a nonconjugated olefinic substrate having a terminal carbon-carbon double bond. The substrate has the formula

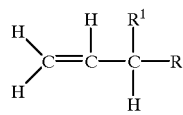

wherein R is selected from the group consisting of —COOH, —COOR$^2$, —CONR$^3$R$^4$, —CN and —CCl$_3$, R$^1$ is selected from the group consisting of —OH, —OCOR$^2$, —NHCOR$^2$ and —NH$_2$, R$^2$ is selected from the group consisting of alkyl, cycloalkyl and aryl and R$^3$ and R$^4$ are independently selected from the group consisting of —H and R$^2$.

The present invention is further directed to a process for the preparation of HMBA. The process comprises free radical addition of methyl mercaptan to 2-hydroxy-3-butenoic acid.

In another embodiment, the present invention is directed to a process for the preparation of methionine. The process comprises free radical addition of methyl is mercaptan to 2-amino-3-butenoic acid.

The present invention is further directed to a process for the preparation of HMBA comprising free radical addition of methyl mercaptan to a non-conjugated olefinic substrate having a terminal carbon-carbon double bond to form a mercaptan addition product. The substrate is selected from the group consisting of esters of 2-hydroxy-3-butenoic acid, 2-hydroxy-3-butenamide, 2-acyloxy-3-butenenitrile and 1,1,1-trichloro-2-hydroxy-3-butene. The process further comprises hydrolyzing the mercaptan addition product to produce HMBA.

Other objects and features of this invention will be in part apparent and in part pointed out hereinafter.

DETAILED DESCRIPTION OF THE PREFERRED EMBODIMENTS

In accordance with the present invention, at has been discovered that mercaptans can be readily added to certain nonconjugated olefinic substrates having a terminal carbon-carbon double bond to produce HMBA, methionine or products readily converted to these valuable animal feed additives. The process involves the free radical addition of a mercaptan across the terminal carbon-carbon double bond of selected substrates.

The nonconjugated olefinic substrates suitable for use in practice of the present invention have the formula

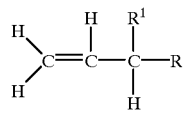

wherein R is selected from the group consisting of —COOH, —COOR$_2$, —CONR$^3$R$^4$, —CN and —CCl$_3$, R$^1$ is selected from the group consisting of —OH, —OCOR$^2$, —NHCOR$^2$ and —NH$_2$, R$^2$ is selected from the group consisting of alkyl, cycloalkyl and aryl and R$^3$ and R$^4$ are independently selected from the group consisting of —H and R$^2$. Generally, R$^1$ can be any common protecting group go long as it does not interfere with the mercaptan addition reaction and can be displaced to produce the desired product. Thus, in addition to the forgoing, R$^1$ may also be siloxy (e.g., —OSi(CH$_3$) or N-silyl (e.g., —N[Si(CH$_3$)$_3$]$_2$). The mercaptan is preferably methyl mercaptan.

Specific examples of nonconjugated olefinic substrates suitable for use in the present invention include: 2-hydroxy-3-butenoic acid, 2-amino-3-butenoic acid, methyl 2-hydroxy-3-butenoate, 2-hydroxy-3-butenamide, 2-acetoxy-3-butenenitrile and 1,1,1-trichloro-2-hydroxy-3-butene. When the desired mercaptan addition product is HMBA, the nonconjugated olefinic substrate is preferably 2-hydroxy-3-butenoic acid. Similarly, when the desired mercaptan addition product is methionine, the nonconjugated olefinic substrate is preferably 2-amino-3-butenoic acid. The use of 2-hydroxy-3-butenoic acid and 2-amino-3-butenoic acid is preferred in the practice of the present invention since HMBA or methionine, respectively, is produced directly upon the free radical addition of methyl mercaptan to the substrate, while the use of other substrates requires one or more additional processing steps after the free radical addition of methyl mercaptan to the substrate to convert the mercaptan addition product to one of these useful products.

The nonconjugated olefinic substrates are either commercially available, or can be readily synthesized by one skilled in the art. For example, the preferred substrate used in the preparation of methionine, 2-amino-3-butenoic acid, is commercially available from Sigma Chemical Company (Saint Louis, Mo.). Alternatively, this preferred substrate may be prepared from acrolein and 4,4'-dimethoxybenzhydrylamine as described by W. J. Greenlee in "Synthesis of β,γ-Unsaturated Amino Acids by the Strecker Reaction", *Journal of Organic Chemistry*, Vol. 49, No. 14, pp. 2632–2634 (1984).

Similarly, 2-acetoxy-3-butenenitrile is commercially available from Aldrich Chemical Company (Milwaukee, Wis.). Alternatively, 2-acetoxy-3-butenenitrile may be synthesized. This synthesis may be carried out by combining acrolein, acetic anhydride and an aqueous solution of sodium cyanide in the presence of a suitable organic solvent (e.g., toluene) and agitating the resulting mixture. After the reaction is complete, the organic layer is separated and purified by contacting it with an aqueous wash (e.g., an aqueous bicarbonate solution) and removing water using a suitable drying agent such as magnesium sulfate. This procedure typically produces about 85% pure 2-acetoxy-3-butenenitrile.

Those skilled in the art can further prepare other suitable substrates from 2-acetoxy-3-butenenitrile. For example, esters of 2-hydroxy-3-butenoic acid can be prepared by hydrolysis of 2-acetoxy-3-butenenitrile. Such hydrolysis may be carried out by mixing the nitrile and a suitable alcohol (e.g., methanol) and heating the mixture to reflux. To this mixture is added a solution of an alcohol saturated with a mineral acid. The resulting mixture is typically allowed to reflux for several hours in order to ensure substantially complete hydrolysis of the nitrile. After cooling and stripping away the alcohol, the hydrolyzate may be washed to remove acidity and dried to remove water. Volatiles can then be removed from the hydrolyzate, and the ester product may be purified by distillation.

The preferred substrate for the preparation of HMBA, 2-hydroxy-3-butenoic acid, can be prepared by hydrolysis of 2-acetoxy-3-butenenitrile. For example, 2-acetoxy-3-butenenitrile can be added to a sulfuric acid solution and the resulting mixture heated for several hours. The resulting hydrolyzate may then be washed with ethyl acetate, and dried using a suitable drying agent such as magnesium sulfate. The pH of the acid product is adjusted and the product collected by removing the ethyl acetate from the hydrolyzate.

Another substrate useful in the practice of the present invention, 1,1,1-trichloro-2-hydroxy-3-butene, may be prepared by the reaction between carbon tetrachloride, chlorotrimethylsilane, magnesium and acrolein, as described by Brunner, et al. in "One Pot Synthesis of Trichloromethyl-Substituted Alcohols", *Journal of Organometallic Chemistry*, Vol. 109, Nos. 1 and 2, pp. C4–C6 (1986), Alternatively, this substrate may be prepared from acrolein through electrolytic anion chain reactions in the presence of carbon tetrachloride and chloroform as described in Japanese patent application Kokai No. 57-126980, published Aug. 6, 1982.

Although the present invention is not limited to any particular theory, it is generally believed that the reaction mechanism for the free radical addition of methyl mercaptan to the nonconjugated olefinic substrate is initiated by a free radical breaking the sulfur-hydrogen bond in methyl mercaptan to produce methyl mercaptan free radical. The methyl mercaptan free radical attacks across the terminal carbon-carbon double bond in the olefinic substrate. This attack results in the double bond being reduced to a single bond and a methylthio group adding according to the Anti-Markovnikov rule at the terminal carbon atom. The unpaired electron on the adjacent, non-terminal carbon atom in the substrate bonds with a hydrogen atom supplied by the methyl mercaptan, thereby creating another methyl mercaptan free radical and continuing the addition cycle.

The process of the present invention can be suitably conducted without a solvent in a batchwise fashion by combining methyl mercaptan and the nonconjugated olefinic substrate in a suitable reactor (e,g., a metal pressure vessel) defining a reaction zone. Alternatively, the methyl mercaptan and nonconjugated olefinic substrate can be combined in a suitable organic solvent in the reaction vessel. In order to control unwanted polymerization, the organic solvent should not be susceptible to radical attack. Preferably, an excess of methyl mercaptan is used to help drive the reaction to completion. The molar ratio of methyl mercaptan to nonconjugated olefinic substrate introduced into the reaction zone is preferably from about 1.1:1 to about 25:1, more preferably from, about 1.1:1 to about 10:1 and especially about 5:1. In order to ease material handling, the methyl mercaptan and nonconjugated olefinic substrate are preferably reacted as liquids. This can be achieved by maintaining appropriate temperature and pressure conditions in the reaction zone.

The free radical addition of methyl mercaptan to the nonconjugated olefinic substrate can be initiated in various ways. For example, a free radical initiator can be introduced into the reaction zone containing the substrate and methyl mercaptan. A suitable free radical initiator is azobisisobutyronitrile (AIBN). Other free radical initiators, such as N-bromosuccinimide (NBS), may also be used to initiate the free radical addition. AIBN is thermally stable at room temperature. However, upon being heated to an activation temperature it produces a free radical which may then start the free radical addition chain reaction described above. When a free radical initiator is employed, the molar ratio of nonconjugated olefinic substrate to free radical initiator introduced into the reaction zone is preferably about 1.5:1 or greater, more preferably from about 1.5:1 to about 100:1, even more preferably from about 25:1 to about 75:1, still more preferably from about 40:1 to about 60.1, and especially about 50:1.

When a temperature activated free radical initiator such as AIBN is employed, the temperature and pressure conditions of the reaction zone are initially maintained so that the reactants are present as liquids and the temperature is below the activation temperature of the free radical initiator. The order of introduction of the reactants and free radical initiator into the reaction vessel is unimportant since the conditions of the reaction zone are such that essentially no reaction occurs.

The reaction zone is then heated above the activation temperature of the free radical initiator using any suitable means (e.g., indirect heat transfer across the wall of the vessel) and the contents of the reaction vessel are agitated (e.g., by shaking the vessel or by stirring the reaction mixture). Preferably, the reaction zone is warmed to a temperature from about 50° C. to about 60° C. to initiate the tree radical addition Preferably, a large portion of the methyl mercaptan remains in the liquid reaction medium as the reaction proceeds. This may be achieved by maintaining appropriate pressure and temperature conditions in the reaction zone as well as by controlling the methyl mercaptan/substrate ratio introduced into the reactor. Preferably, the pressure in the reactor is maintained from about 55 psig to about 65 psig. Alternatively, the methyl mercaptan may be fed into the liquid reaction medium within the reactor at a rate at least sufficient to balance the consumption of methyl mercaptan in the free radical addition reaction. In a further alternative, the reaction vessel may be equipped with a reflux condenser. In such an arrangement, the methyl mercaptan may be allowed to substantially volatilize as the reaction zone is heated above the activation temperature. The methyl mercaptan vapors are condensed and the liquid returned to the reaction mixture, In an alternative embodiment, an ultraviolet light source is used in place of a chemical agent to initiate the free radical addition of methyl mercaptan to the substrate. For example, a reaction vessel having a translucent portion (e.g., a reactor window) may be employed and one or more sources of ultraviolet light (e.g., a broad band ultraviolet lamp) directed into the translucent portion of the vessel to expose the reaction zone to ultraviolet light. Alternatively, the ultraviolet light source may be disposed within a translucent envelope extending into the reaction vessel. Preferably, the reaction zone is radiated from all sides by such an ultraviolet light source.

After the reaction is complete (typically about 5 hours), the reaction mass is cooled to room temperature and excess methyl mercaptan is allowed to volatilize and is removed from the reaction vessel. Preferably, excess methyl mercaptan is recovered for reuse.

As noted above, use of 2-hydroxy-3-butenoic acid and 2-amino-3-butenoic acid as the nonconjugated olefinic substrate is preferred in the practice of the present invention since HMBA or methionine, respectively, are produced directly upon addition of methyl mercaptan to the substrate. However, if one of the other nonconjugated olefinic substrates is employed, the mercaptan addition product obtained may be converted to HMBA or methionine through one or more additional processing steps. For example, it the substrate is an alkyl, cycloalkyl or aryl ester of 2-hydroxy-3-butenoic acid, 2-hydroxy-3-butenamide, 2-acyloxy-3-butenenitrile or 1,1,1-trichloro-2-hydroxy-3-butene, the addition product is converted to HMBA by hydrolysis. This further processing can be readily achieved by one skilled in the art. For example, the mercaptan addition product can be suitably hydrolyzed to HMBA by mixing it with an equal amount of sulfuric acid (typically about a 50% solution) and maintaining the resulting mixture at about 60° C. for about 5 hours. As one skilled in the art would recognize, alternative acids and conditions may be used to perform the additional hydrolysis step. Similarly, in the preparation of methionine, —NHCOR$^2$ at R$^1$ may be converted to —NH$_2$ by hydrolysis s. If substrates in which R$^1$ is selected to be siloxy or N-silyl are employed, these protecting groups can be converted to the desired substituent using standard methods known to those skilled in the art.

Although the process of the present invention may be conducted in a batchwise fashion as described above, it should be understood that by appropriate modification, the free radical addition of methyl mercaptan to the nonconjugated olefinic substrate and processing of the addition product (if necessary) may be conducted in a semibatch or continuous fashion.

The present invention is illustrated by the following examples which are merely for the purpose of illustration and are not to be regarded as limiting the scope of the invention or manner in which it may be practiced.

EXAMPLE 1

In this Example, 2-acetoxy-3-butenenitrile was prepared.

A 1000 milliliter, 4 necked round-bottom flask that was flame dried under nitrogen, was cooled to −11° C. with an ethylene glycol/dry ice mixture. To this flask, a magnetic stirrer, acrolein (0.091 moles) and toluene (150 milliliters) were added. Acetic anhydride (0.77 moles) was added to the mixture dropwise over a period of about 7–8 minutes. During this addition, the temperature of the mixture increased to about −6° C. Next, sodium cyanide (1.12 moles) was dissolved in water (280 milliliters). The sodium cyanide solution was added to the mixture over a period of about 2 hours, and the temperature increased to about 3° C. The mixture was then stirred for an additional 2 hours, and the temperature increased to about 8° C. The resulting mixture was placed in a separation funnel, and the organic layer was separated. The water layer was washed with two solutions of toluene (50 milliliters each). The toluene solutions and the original organic layer were combined, and washed with sodium bicarbonate and water and dried over magnesium sulfate. The magnesium sulfate was filtered off, and the organic layer was then distilled and product was collected between 36° C. and 38° C. Nuclear magnetic resonance analysis showed the product to be almost pure 2-acetoxy-3-butenenitrile.

EXAMPLE 2

In this Example, 2-hydroxy-3-butenoic acid was prepared from 2-acetoxy-3-butenenitrile.

In a 500 milliliter round-bottom flask containing a magnetic stirrer, sulfuric acid (30 milliliters of 98% solution) was slowly added to water (30 milliliters) After twenty minutes, 2-acetoxy-3-butenenitrile (20 grams) was added dropwise to the acid water mixture over about a 10 minute period. The mixture was allowed to react for about six hours. Next, ethyl acetate (75 milliliters) was added, and a third layer formed. The organic layer was separated and mixed with ethyl acetate (75 milliliters). This mixture was dried with magnesium sulfate, and the ethyl acetate was stripped off at 45° C. and 10 mm Hg. The pH of this solution was adjusted to 1.1 with sulfuric acid, and extracted with two aliquots of ethyl acetate (75 milliliters each). The organic layer was then dried over magnesium sulfate, and the ethyl acetate was strapped off at 45° C. and 10 mm Hg. Gas chromatography/mass spectrophotometry confirmed that the product was at least ?76% 2-hydroxy-3-butenoic acid.

EXAMPLE 3

In this Example, HMBA was prepared by the free radical addition of methyl mercaptan to 2-hydroxy-3-butenoic acid.

In a 10 milliliter round-bottom flask fitted with a dry ice condenser, 2-hydroxy-3-butenoic acid (4 milliliters) was mixed with methyl mercaptan (2–3 milliliters. This mixture was illuminated with a HANOVIA brand broad band ultraviolet light to initiate the free radical addition. As the reaction proceeded, volatilized methyl mercaptan was returned to the reaction medium with the aid of the dry ice condenser. After about six hours, the resulting product was allowed to stand at room temperature for about 12 hours to allow excess methyl mercaptan to evaporate. Analysis by nuclear magnetic resonance showed a considerable amount of HMBA.

EXAMPLE 4

In this Example, methyl 2-hydroxy-3-butenoate was prepared from 2-acetoxy-3-butenenitrile.

In a 200 milliliter, 3 necked round-bottom flask with a magnetic stirrer, anhydrous methanol (1.06 moles) and 2-acetoxy-3-butenenitrile (0.04 moles) were combined and heated to reflux. The heating bath was removed and a mixture of methanol (1.06 moles) saturated hydrochloric acid and concentrated hydrochloric acid (11 milliliters of 36% solution) was added at such a rate so as to continue reflux. After the exothermic reaction had subsided, heat was applied and the mixture was refluxed for another 2 hours. Next, the heat was removed, and HCl gas was swept over the solution for a period of 1.5 hours, causing the mixture to reflux without heat. After 1.5 hours, heat was reapplied, and the mixture refluxed for another 2.5 hours. The mixture was then cooled to room temperature, and the methanol was stripped off at 50° C. and 20 mm Hg. A solid which had formed was determined by NMR not to be desired product and was filtered off and discarded. The filtrate was mixed with diethyl ether (50 milliliters) and washed with an aqueous solution of potassium hydroxide until the acidity of the mixture was neutralized. Next, the mixture was washed with ammonium bicarbonate and dried over magnesium sulfate. The magnesium sulfate was filtered off, and the ether was stripped off at room temperature and 15 mm Hg. This produced a crude ester compound.

The crude ester was placed in a 50 milliliter round bottom flask under 52 mm Hg at room temperature. The solution was then distilled through a six inch distillation column, with product being collected from 86° C. to 152° C. Gas chromatography showed the collected fractions to be 98% pure methyl 2-hydroxy-3-butenoate.

EXAMPLE 5

In this Example, methyl 2-hydroxy-4-(methylthio) butanoate was prepared by the free radical addition of methyl mercaptan to methyl 2-hydroxy-3-butenoate, the methyl ester of 2-hydroxy-3-butenoic acid, The free radical addition of methyl mercaptan to the ester substrate was conducted in a metal reaction vessel. Under pure, dry nitrogen, the reaction vessel was cooled with liquid nitrogen to −78° C. and then charged with methyl 2-hydroxy-3-butenoate (0.7 grams), methyl mercaptan (2–3 milliliters) and a tree radical initiator (AIBN, 0.014 grams). Temperature and pressure probes were inserted in the reaction vessel and the reaction vessel was sealed and wrapped with heating tape. The reaction vessel was then placed on a shaker and the reaction vessel and its contents were agitated and warmed using heat supplied by the heating tape. The reaction was allowed to proceed for 5 hours at a temperature between 50° and 60° C. and a pressure of 50 to 70 psig, After 5 hours, heating was discontinued and the reaction vessel and its contents were allowed to cool to room temperature. Unreacted methyl mercaptan was allowed to evaporate from the reaction mixture for twelve hours. Gas Chromatography analysis of the reaction mixture indicated an 85% yield of methyl 2-hydroxy-4(methylthio) butanoate.

The methyl 2-hydroxy-4(methylthio)butanoate could easily be hydrolyzed by one skilled in the art to HMBA. For example, the 2-hydroxy-4(methylthio)butanoate could be mixed with an equivalent amount of sulfuric acid (50% solution) and the mixture heated to 60° C. for 5 hours. After cooling to room temperature, the pure HMBA is collected by distillation.

In view of the above, it will be seen that the several objects of the invention are achieved. As various changes could be made in the above-described processes without departing from the scope of the invention, it is intended that all matter contained in the above description be interpreted as illustrative and not in a limiting sense.

What is claimed is:

1. A process for the preparation of a mercaptan addition product comprising free radical addition of methyl mercaptan to a nonconjugated olefinic substrate having a terminal carbon-carbon double bond, the substrate having the formula

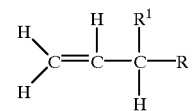

wherein R is selected from the group consisting of —COOH, —COOR$^2$, —CONR$^3$R$^4$, —CN and —CCl$_3$, R$^1$ is selected from the group consisting of —OH, —OCOR$^2$, —NHCOR$^2$ and —NH$_2$, R$^2$ is selected from the group consisting of alkyl, cycloalkyl and aryl and R$^3$ and R$^4$ are independently selected from the group consisting of —H and R$^2$.

2. The process set forth in claim 1 wherein methyl mercaptan and the nonconjugated olefinic substrate are combined in a reaction zone, the molar ratio of methyl mercaptan to substrate introduced into the reaction zone being from about 1.1:1 to about 25:1.

3. The process set forth in claim 2 wherein methyl mercaptan and the nonconjugated olefinic substrate are combined in the reaction zone in the presence of a free radical initiator to initiate the free radical addition of methyl mercaptan to the substrate.

4. The process set forth in claim 3 wherein the free radical initiator is azobisisobutyronitrile.

5. The process set forth in claim 3 wherein the molar ratio of nonconjugated olefinic substrate to free radical initiator introduced into the reaction zone is from about 1.5:1 to about 100:1.

6. The process set forth in claim 2 wherein the reaction zone is exposed to ultraviolet light to initiate the free radical addition of methyl mercaptan to the nonconjugated olefinic substrate.

7. The process as set forth in claim 1 wherein the nonconjugated olefinic substrate comprises 2-hydroxy-3-butenoic acid such that the mercaptan addition product comprises 2-hydroxy-4-(methylthio)butanoic acid.

8. The process as set forth in claim 1 wherein the nonconjugated olefinic substrate comprises 2-amino-3-butenoic acid such that the mercaptan addition product comprises methionine.

9. A process for the preparation of 2-hydroxy-4-(methylthio)butanoic acid, the process comprising free radical addition of methyl mercaptan to 2-hydroxy-3-butenoic acid.

10. A process for the preparation of methionine, the process comprising free radical addition of methyl mercaptan to 2-amino-3-butenoic acid.

11. A process for the preparation of 2-hydroxy-4-(methylthio)butanoic acid, the process comprising free radical addition of methyl mercaptan to a nonconjugated olefinic substrate having a terminal carbon-carbon double bond to form a mercaptan addition product, the substrate selected from the group consisting of esters of 2-hydroxy-3-butenoic acid, 2-hydroxy-3-butenamide, 2-acyloxy-3-butenenitrile and 1,1,1-trichloro-2-hydroxy-3-butene; and hydrolyzing the mercaptan addition product to produce 2-hydroxy-4-(methylthio)butanoic acid.

* * * * *

UNITED STATES PATENT AND TRADEMARK OFFICE
CERTIFICATE OF CORRECTION

PATENT NO : 5,973,200
DATED : October 26, 1999
INVENTOR(S): Karl E. Koenig

It is certified that error appears in the above-identified patent and that said Letters Patent is hereby corrected as shown below:

In column 1, the "MMP" and "HMBN" labels within the reaction sequence are not below the appropriate chemical structure. Please position the labels as indicated below:

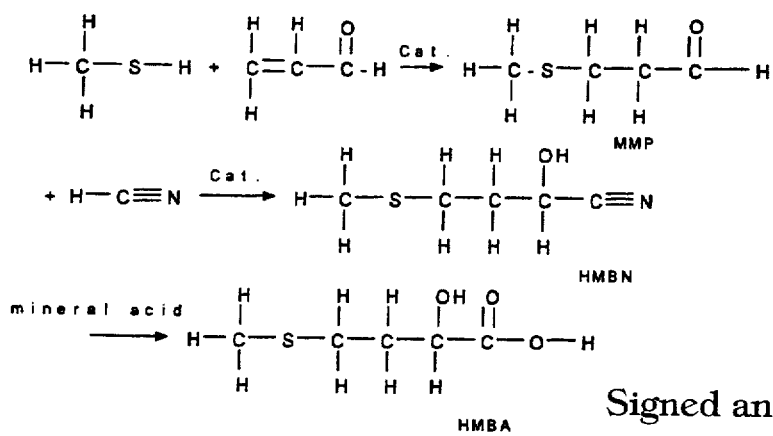

Signed and Sealed this

Thirtieth Day of May, 2000

*Attest:*

Q. TODD DICKINSON

*Attesting Officer*        *Director of Patents and Trademarks*